US007962435B2

(12) United States Patent
Yu et al.

(10) Patent No.: US 7,962,435 B2
(45) Date of Patent: Jun. 14, 2011

(54) SYSTEM ARCHITECTURE AND PROCESS FOR SEAMLESS ADAPTATION TO CONTEXT AWARE BEHAVIOR MODELS

(75) Inventors: Juan Yu, Cranbury, NJ (US); Hasan Timucin Ozdemir, Plainsboro, NJ (US); Kuo Chu Lee, Princeton Junction, NJ (US)

(73) Assignee: Panasonic Corporation, Osaka (JP)

( * ) Notice: Subject to any disclaimer, the term of this patent is extended or adjusted under 35 U.S.C. 154(b) by 745 days.

(21) Appl. No.: 12/034,164

(22) Filed: Feb. 20, 2008

(65) Prior Publication Data
US 2009/0210373 A1 Aug. 20, 2009

(51) Int. Cl.
G06F 17/00 (2006.01)
G06N 5/02 (2006.01)
G08B 13/00 (2006.01)

(52) U.S. Cl. ............... 706/47; 706/45; 706/46; 340/541; 348/143

(58) Field of Classification Search .................... 706/47; 348/143; 434/236
See application file for complete search history.

(56) References Cited

U.S. PATENT DOCUMENTS

| 7,667,596 B2 * | 2/2010 | Ozdemir et al. ............... 340/541 |
| 2002/0029208 A1 | 3/2002 | Josephson |
| 2006/0047789 A1 | 3/2006 | Kumar et al. |
| 2006/0059253 A1 | 3/2006 | Goodman et al. |
| 2006/0064503 A1 | 3/2006 | Brown et al. |
| 2006/0101037 A1 | 5/2006 | Brill et al. |

OTHER PUBLICATIONS

W. Hu, T. Tan, L. Wang, S. Maybank: "A Survey on Visual Surveillance of Object Motion and Behaviors"; IEEE Transactions on Systems, Man and Cybernetics, Part C, vol. 34, Issue 3, p. 334-352 (Aug. 2004).*
Robert Collins et al.; "A System for Video Surveillance and Monitoring: VSAM Final Report"; CMU-RI-TR-00-12, CMU (2000) 69 pages.*
Cai et al, "Tracking Human Motion in Structured Environments using a Distributed-Camera System", IEEE Transactions on Pattern Analysis and Machine Intelligence, vol. 21, No. 12, Nov. 1999 pp. 1241-1247.*

* cited by examiner

Primary Examiner — Jeffrey Gaffin
Assistant Examiner — Ola Olude-Afolabi
(74) Attorney, Agent, or Firm — Harness, Dickey & Pierce, P.L.C.

(57) ABSTRACT

A surveillance system implements an architecture and process to support real-time abnormal behavior assessment operations in a distributed scalable sensor network. An automated behavior model builder generates behavior models from sensor data. A plurality of abnormal behavior scoring engines operating concurrently to generate abnormal behavior assessment models by scoring the behavior models. An execution performance manager performs fast switching of behavior models for the abnormal behavior scoring engines. The execution performance manager performs detection of abnormal behavior score distribution characteristic deviation by comparing a current abnormal behavior assessment model to a pre-recorded abnormal behavior assessment model. The execution performance manager selects a pre-recorded behavior model for the abnormal behavior scoring engines when the deviation exceeds a predetermined threshold.

31 Claims, 4 Drawing Sheets

SYSTEM ARCHITECTURE AND PROCESS FOR SEAMLESS ADAPTATION TO CONTEXT AWARE BEHAVIOR MODELS

FIELD

The present disclosure generally relates to surveillance systems, and relates in particular to an abnormal behavior assessment system that automatically learns and adapts to changing behavior patterns.

BACKGROUND

The statements in this section merely provide background information related to the present disclosure and may not constitute prior art.

A large area video sensor network requires efficient coordination of data collected and analyzed by a multiple set of analysis and detection algorithms. The analysis algorithm collects data and builds one or more behavior models for the detection algorithm to perform scoring and fusion functions. These algorithms are often CPU intensive, embedded in the device, and specifically modeled and configured for a fixed camera view.

Low CPU and data processing efficiency results in several limitations. For example, video analysis algorithms are CPU intensive. Also, processing all of the video streams for multiple camera systems is prohibitively expensive. Furthermore, abnormal behavior is hard to define and often hides within the normal data. Yet further, the video analysis algorithms yield very low detection accuracy especially when the motion and background pattern changes in the field of view (FOV) of the camera.

Additional limitations result from a fixed local context. For example, most surveillance systems focus on fixed camera views and/or fixed sensor positions. But when contexts change, the video analysis algorithm needs to adapt to the change quickly. The context has multiple levels of detail. At the image level, lighting and focus needs to be adapted. At the image analysis level, the background analysis model needs to be adapted. Adapting to a new background can be processed using image recognition techniques or using preset models corresponding to the camera views. In the behavior analysis model level, the object motion and background model needs to be adapted simultaneously. The problem of adapting to a new behavior model for abnormal behavior assessment is more complicated because the behavior model of long motion trajectory and human behavior may take a long time to establish and is application and context dependent.

Limitations also result from a lack of context awareness. For example, the surveillance algorithm often runs in a place that is close to the camera to reduce the communication cost. But for a large scale video sensor network, sensor data needs to be fused based on temporal and spatial relationship to obtain a global understanding of the activities. Therefore, having the analytic engine close to the camera does not necessarily solve the dynamic loading and execution of models and fusion engines that are required to adapt to the changing contexts and applications cross multiple cameras.

Further limitations result from implementation as a closed system. For example, an open source computer vision algorithm library is typically compiled and bound to a fixed application and runs in a dedicated machine for a fixed set of cameras. In other words, there is no open interface to support the exchange of a binary library and models to support exchange of proprietary algorithms to track events that cross over multiple geographically distributed areas and administration entities.

Yet further limitations result from a lack of interoperability between analytic systems. For example, surveillance systems work in isolation. Therefore, the models built by surveillance system for different contexts are different and cannot be exchanged quickly to achieve higher efficiency and productivity in model building.

Limitations of today's surveillance systems are readily appreciated with reference to the following example, in which the problem is to accomplish model re-use and sharing within one camera and between cameras. For example, the security guard will change the settings of a PTZ camera due to some investigation and cannot leave the camera to the exact same configuration. In this case, the FOV of the camera changes. The system can prefer not to generate alarms until the online model builder builds a mature model (e.g., prevention of spurious alarm generation). Today's systems are limited because they cannot re-use some part of the previously built models, such as models previously produced by the same camera or by a second camera that has an overlapped field of view with the first camera. As a result, today's systems are not able to evaluate alarm conditions by using partial model data retrieved from the second camera.

Problems caused by these limitations are particularly evident with reference to an example involving multi-purpose rooms (such as big lobbies). In such rooms, the site can have different usages such as for special events. For example, in the case that a temporary reception desk is installed in the area, the usage of the site is changed, which causes false alarms even though the field of view of the camera has not changed. The false alarms are generated because the site usage has been changed and the current model does not capture the change yet. Today's surveillance systems are capable of suppressing the alarms by detecting that the alarm generation is somewhat increased and that the alarms are not acknowledged. However, these systems still initially generate false alarms and later fail to issue genuine alarms. This limitation results from inability of these systems to allow users to share common behavior models and develop multiple, different types of assessment criteria using multiple, user defined scores and score fusion functions such as aggregation and normalization. In other words, today's surveillance systems are not able to summarize a behavior model, query based on the summarization, and receive in response one or more closely matching previously generated models efficiently. As a result, these systems are not able to use such a model for behavior assessment and evaluation, employ an online model builder to share and start revising shared models collaboratively, and develop useful behavior scoring and fusion engines that can also be shared instead of trying to learn from scratch and work in isolation.

Still further limitations result from the inability of today's models to associate motion behavior with multiple different object types based on features extracted from real-time observations without knowing what the objects actually are (i.e, a person, a car, and a truck). For the purpose of detecting abnormal behavior and generate alert, it is not necessary to identify the objects. For example, if the system does not distinguish the moving object type to build models, the behavior detection generates false alarms and misses alarms. For instance, in a traffic scenario, a camera observes an intersection at which persons, cars, and trucks are expected to exhibit different behaviors. For example, pedestrians are expected to use the crosswalk and sidewalks and the speed of which may be slower than the car along the road but faster than the car in the pedestrian crossing. In a warehouse environment, forklift motion is different from workers. For safety reason, alert may be generated when person and forklift are getting too close. When warehouse lay out changes, or the goods in the docking area fills up the behavior of the forklift and workers are different. Therefore, to detect abnormal behavior different models learned in the past may be tested and used to control the amount of the false alarms. When the moving object type is not considered with the motion model, the system cannot automatically detect: (a) person walking/running on the road instead of on the crosswalk and/or the side walk; (b) a vehicle driving on the side walk; (c) a truck driving in the no-truck lane, etc. The inability of today's surveillance systems to handle different object types is caused in part by failure to associate the model with an appearance model. In other words, the systems cannot build object type specific models and execute behavior analyses based on these object type models. It should be noted that building object type specific models based on appearance models does not require recognition of specific object type/classification.

Yet more limitations of today's surveillance systems exist. For example, many of today's surveillance systems do not store models in a decentralized manner (locally by each camera). Also, today's models are not searched (peer2peer search). Further, today's models are not predictive (in case of a panning camera controlled by a script). As a result, today's surveillance systems lack scalability.

For the reasons detailed above, most of today's video analytic systems build statistical models for the background and motion flow patterns. Regarding these models, there are many different models built by different algorithms tailored for different application and environments. Current state of the art systems do teach how to adapt to preset camera PTZ position change and background image changes. However, for the end user, it takes time and effort for selecting and fixing and preset the camera views, selecting algorithms, building the statistical model, and tuning the configuration parameters to achieve acceptable performance. It is unlikely that user can remember and which model and algorithm to use and be able to learn and switch the behavior model in real-time.

Therefore, process and architectures to support behavior model level sharing and fast switching is an open area for surveillance system design that needs further work.

SUMMARY

A surveillance system implements an architecture and process to support real-time abnormal behavior assessment operations in a distributed scalable sensor network. An automated behavior model builder generates behavior models from sensor data. A plurality of abnormal behavior scoring engines operating concurrently to generate abnormal behavior assessment models by scoring the behavior models. An execution performance manager performs fast switching of behavior models for the abnormal behavior scoring engines. The execution performance manager performs detection of abnormal behavior score distribution characteristic deviation by comparing a current abnormal behavior assessment model to a pre-recorded abnormal behavior assessment model. The execution performance manager selects a pre-recorded behavior model for the abnormal behavior scoring engines when the deviation exceeds a predetermined threshold.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

A novel surveillance system architecture and process improves abnormal behavior assessment accuracy and scalability. The novel system achieves efficient adaptation by building local and global context maps that support the fast construction, exchange, and search of backgrounds and motion pattern models between devices efficiently. The new surveillance system architecture and process is designed to support automated and seamless adaptation of changing application and environment contexts.

In some embodiments, the new architecture and process has a model building module receiving moving object data, generating a current behavior model from the moving object data, and storing the current behavior model by indices for at least one spatial-temporal attributes, at least one content summary attribute and at least one partial description of the content of the model. Some embodiments also store the current behavior model by indices for a user defined special event descriptor. A set of scoring engine modules receives the moving object data, loads a previously stored model, and uses it as reference model to generate sequences of current scores against a separate reference model that is different from the current model being built in real time. The scoring engine modules generate a statistical summary of the sequences of scores for one or more of the moving objects, and stores the current scores and statistics in the model data store in correlation with the current model.

An execution performance manager monitors the execution of the scoring engines by comparing the statistics of the current scores with score statistics previously stored in the reference model. The execution performance manager also retrieves previously generated score statistics and determines whether a significant change has occurred by performing an analysis of the current scores and the previously generated scores. Contingent upon determination that a significant change has occurred, the execution performance manager retrieves a previously stored model as the second reference model based on similarity of temporal-spatial descriptor, content description of the model, and partial content stored in the current model. It also generates behavior scores against the second reference model in parallel. If the score statistics of the new reference model match the previously stored score statistics, the scores from the second reference model are used instead of the first reference model in use. This similarity based model retrieval, and parallel evaluation of scores, and selection of the model based on score distribution achieves seamless and fast environment and application context adaptation.

Figure 1:
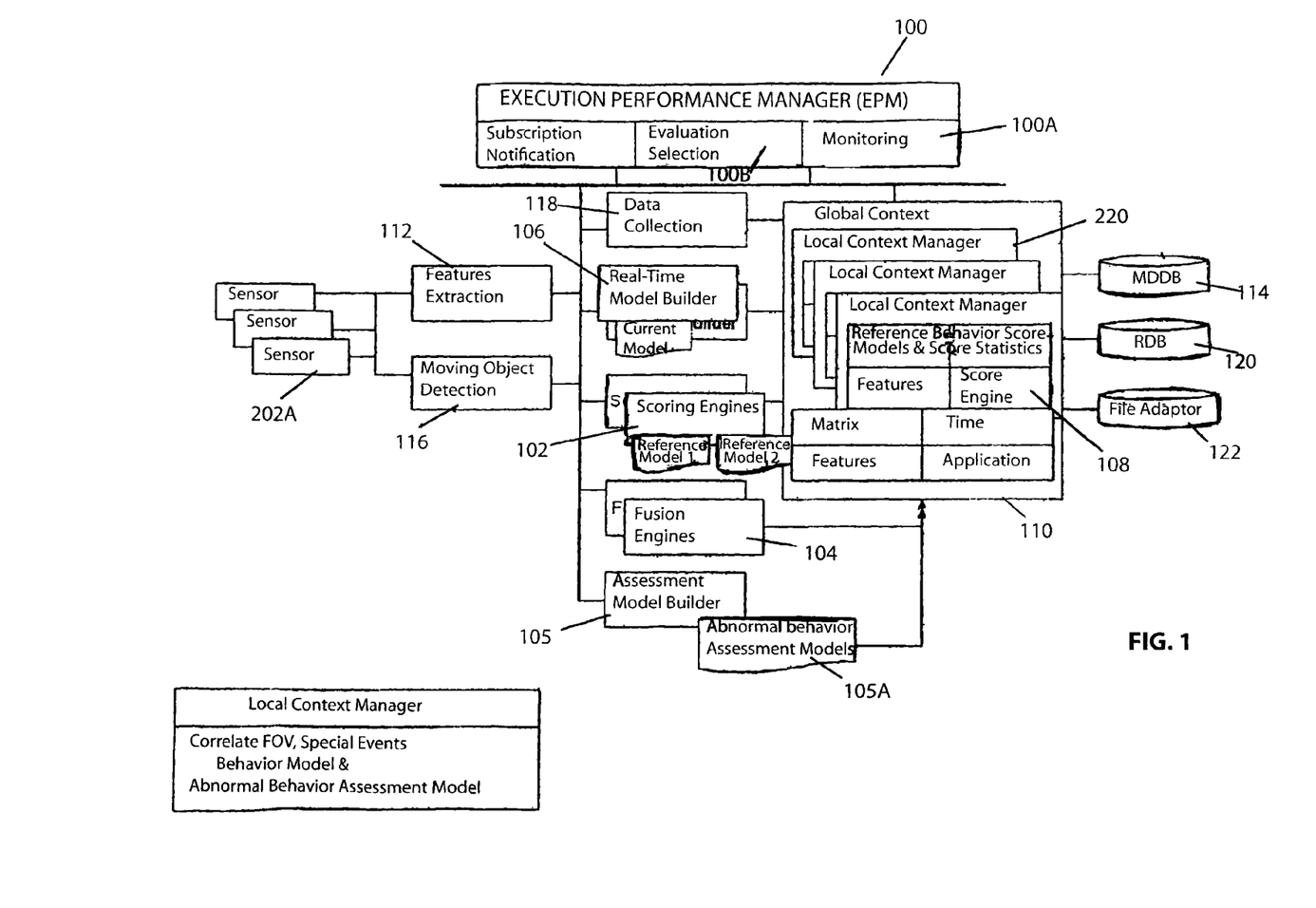
FIG. 1 is a block diagram illustrating a system architecture for a system architecture for seamless adaptation to context aware behavior models.

Referring to FIG. 1, the system architecture includes an execution performance manager (EPM) 100 that controls the adaptation to changing application contexts such as backgrounds, models, algorithms and applications. The Monitoring Module 100A in EPM 100 monitors the execution of a set of Scoring algorithm Engines (SEs) 102 and Fusion algorithm Engines (FEs) 104 against corresponding models learned from a Real-Time Model Builder (RMB) 106. The Evaluation and Selection Module 100B in EPM 100 uses a preset Efficiency and Accuracy Goals and scoring statistics incorporated in each model to trigger the adaptation process and to decide how to adapt to changing context by selecting the best matching local context (LTXT) 108 and global application context (GTXT) 110.

EPM 100 uses multiple learning algorithms to make adaptation decisions. Upon the decision of EPM 100, a new set of configurations and instances of SEs 102, FEs 104, and Models (SE/FE/M) are scheduled to run in parallel to the previously running set of SEs/FEs/Models. The outputs from both previous and new sets of SE/FE are processed concurrently to result in a smooth transition. EPM 100 compares the performance and accuracy goal by monitoring the statistical and ranking of output variables of SEs/FEs for multiple applications. The output variables include abnormal behavior scores obtained by aggregating a sequence of individual scores of motion trajectory against a reference model. Furthermore the statistics of the aggregated scores of a set of input objects are aggregated to form a behavior assessment model 105A. The behavior assessment model is used to represent the behavior score statistics. The assessment model (behavior score statistics) is correlated with the reference model, field of view of the camera or sensor, feature set of the objects, and other parameters to facilitate the model switching decisions.

The system architecture includes additional components. For example, Features Extraction Module 112 extracts behavior model features, behavior score statistics (summarized in abnormal behavior assessment model), motion trajectory patterns, color feature and shape feature, and other Mpeg7 related features from the input moving objects. These features are stored in the Multidimensional Data Base (MDDB) 114 and a reference of the features set in Multidimensional Data Base is archived in Local Context 108. The MDDB can perform a fast, multi-dimensional search operation based on an L2 distance calculation on a reduced set of features from the original feature sets. Additionally, Moving Object Detection Module 116 sends metadata of moving objects, such as object ID, center of position of object and blob of object information to Model Builder 106 and Scoring Engine 102. Further, Data Collection Module 118 communicates with Moving Object Detection Module 116 to get metadata, parses the metadata, sends parsed data to scoring engine 102, and saves the data into Relational Data Base 120. The reference model and the score statistics are saved in either file adaptor or RDB based on application preferences. The copy of model built in real-time by model builder is called current model. The current model is not used by scoring engines because complex behavior often requires a long time to accumulate a large set of object motion trajectories. The scoring engines use a reference model that is built by the model builder previously. When a context changes or application changes occur, a second reference model is loaded and used by scoring engine to generate second set of scores in parallel with the score generated against the first reference model in use to achieve rapid and seamless model switching automatically without user intervention. The real-time scoring operation is not stopped and some of the abnormal scores may be executed against the new reference model and the statistics of which will be correlated with the new model.

Real-Time Model Builder 106 is an Online Model Builder that generates models through executing different algorithms based on the real time metadata from Moving Object Detection Module 116 or from previous collected data stored in Relational Data Base 120. Model builder can invoke multiple types of algorithms to build different types of models for different applications. For example, it can produce a model that captures the lower level statistics, such as moving objects' motion flow patterns and object features. This type of model is called the motion object behavior model. Motion object behavior model is used by scoring engine to generate a sequence of abnormal behavior scores. The content based features used as indices of all the models are stored in MDDB 114 and cached in Local Context 108 located in the main memory of a computer. The Local Context 108 links the models with the moving object's multidimensional features set stored in MDDB 114.

Scoring Engine 102 continuously receives the metadata. It supports the scoring of the input meta data of the motion object on multiple reference models. It invokes a Scoring Engine library to score each moving object. Scoring Engine also aggregates the scoring results and saves the results into the Relational Data Base 120. It also keeps the trajectory information of each moving object in runtime.

Fusion engine 104 performs high level scoring against the abnormal behavior scoring model for each motion trajectory in a fixed time interval. The references of abnormal behavior scores, assessment model, and assessment scores are stored in Relational Data Base and cached in Local Context 108. The key features of abnormal behavior assessment model are extracted into multi-dimensional array and stored in MDDB for fast retrieval. The system supports dynamically loaded model builder to build an abnormal behavior assessment model based on the summarized statistical characteristics of maximal and mean abnormal behavior scores for all the trajectories. This enables the representation of abnormal behavior detection application context to be defined by abnormal scoring engine outputs and the statistical summary model of the outputs. This specific context representation is used to trigger model change and to speed up model selection processes. Data Bases store different kinds of data. For example, Multidimensional Data Base (MDDB) 114 stores the multi-dimensional feature vectors. In contrast, Relational Data Base (RDB) stores the model descriptor, binary models, scores, aggregation score, and motion object meta data. Another Data Base, File Adaptor 122, stores the Scoring engines' and Fusion engines' configuration files and model templates.

Assessment Model Builder builds the assessment model, which captures a statistical behavior score pattern within a certain time frame. The assessment model represents the collective statistics of all the abnormal behavior score in a time interval against the low level motion object behavior model. This type of model is called the abnormal behavior score statistics. A motion object abnormal behavior can be defined by a collection of abnormal behavior scores obtained from multiple scoring engines. Therefore, it is called user-defined abnormal behavior assessment against a common low level motion behavior model. An example of the low level motion object behavior model design captures the statistics of a moving objects' spatial and temporal information. The assessment models are cached in Local Context 108. The assessment models are used by EPM 100 to make the decision on application context switch.

Local context (LTXT) 108 is a set of mappings defining:
Context→recommended SE/FE/Models
where context is a tuple containing parameters such as: (Context ID, TimeProperty, SpaceProperty, ApplicationProperty, Cached Reference Models, Cached score and assessment model, links to the models and indices in the databases). Local Context Manager 220 manages Local Context, and creates the data structure depicted in FIG. 3

Figure 3:
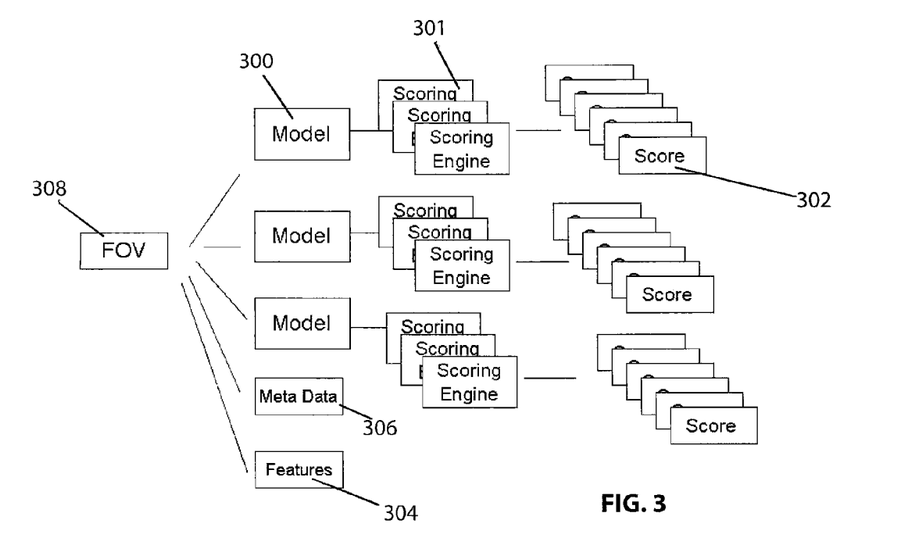
FIG. 3 is a block diagram illustrating a data model correlating models to FOV, scores, features, and time information.

FIG. 3 depicts the detail of data structure for Local Context. Each of field of view (FOV) has its unique context characteristics. The context ID in Local Context is represented by a FOV 308. There are multiple Models 300 built for the FOV 308. The multiple models include motion object behavior models for the different time frame and the different location within the FOV and abnormal behavior assessment models 105*a* generated from Assessment Model Builder 105 based on the scores from Scoring Engine 102 and Fusion Engines 104. The metadata 306 captures the time information (TimeProperty), space information (SpaceProperty) and configuration data about the FOV 308. The Features 304 captures the features such as color feature, shape feature and other Mpeg7 features extracted from motion objects detected from the FOV 308. Since each FOV contains the different motion objects behaviors, therefore each FOV has a set of scoring engines libraries. The set of scoring engine libraries 301 are for capturing the behaviors of the FOV 308 and are dynamically loading to the system when the system is started up and run as Scoring Engine 102 indicated in FIG. 1. Each scoring engine generates lots of scores against the behavior model for each moving point of an object. It is difficulty to store and visualize them. So the scoring engine aggregates the scores and captures in Score 302 instead of outputting the raw scores.

Local Context Manager 220 supports fast access to most likely or similar models based on motion patterns and partially built motion models cached in Local Context. The fast search is accomplished by an in memory MDDB function. The MDDB provides a similarity search and returns multiple reference models that can be potentially used by the EPM. The content based similarity provides new types of locality of reference properties beyond the typical spatial-temporal locality property typically adopt by paging systems in operating system and web browsers. The motion content based locality of a reference captures sudden motion behavior pattern changes that cannot be captured by gradual temporal and spatial pattern shift. For example, when a typical flow is detoured or a special event happens, the detour and special event patterns may be already learned in the past. Therefore, the system can retrieve these previously built reference models to continue detecting abnormal behavior without waiting for model builder to build a completely new model, which would take a relatively long time Global Context (GTXT) 110 is made up of one or more transformation relationships and probability dependency mapping between the LTXT 108 in space, time, and application. For example, if two cameras are monitoring a passage between two areas, with overlapped views, then the GTXT 110 contains the transformation matrix for the overlapped FOV. The transformation matrix is provided by an automated or manual camera calibration system. The matrix is used to convert the geometry of the reference model learned from one camera to the new geometry that can be used by the scoring engines of the second camera. The architecture and process allows for fast collaboration between scoring engines by using MDDB to search for a model based on partial FOV. When a behavior pattern change happens in between two camera overlapped FOV region, the system can quickly search the partial model in the overlapped regions to transform the model to a physical geometry references from the local coordinate of the camera. The transformed model can be shared and compared in real-time to support abnormal behavior assessment across cameras.

Figure 5:
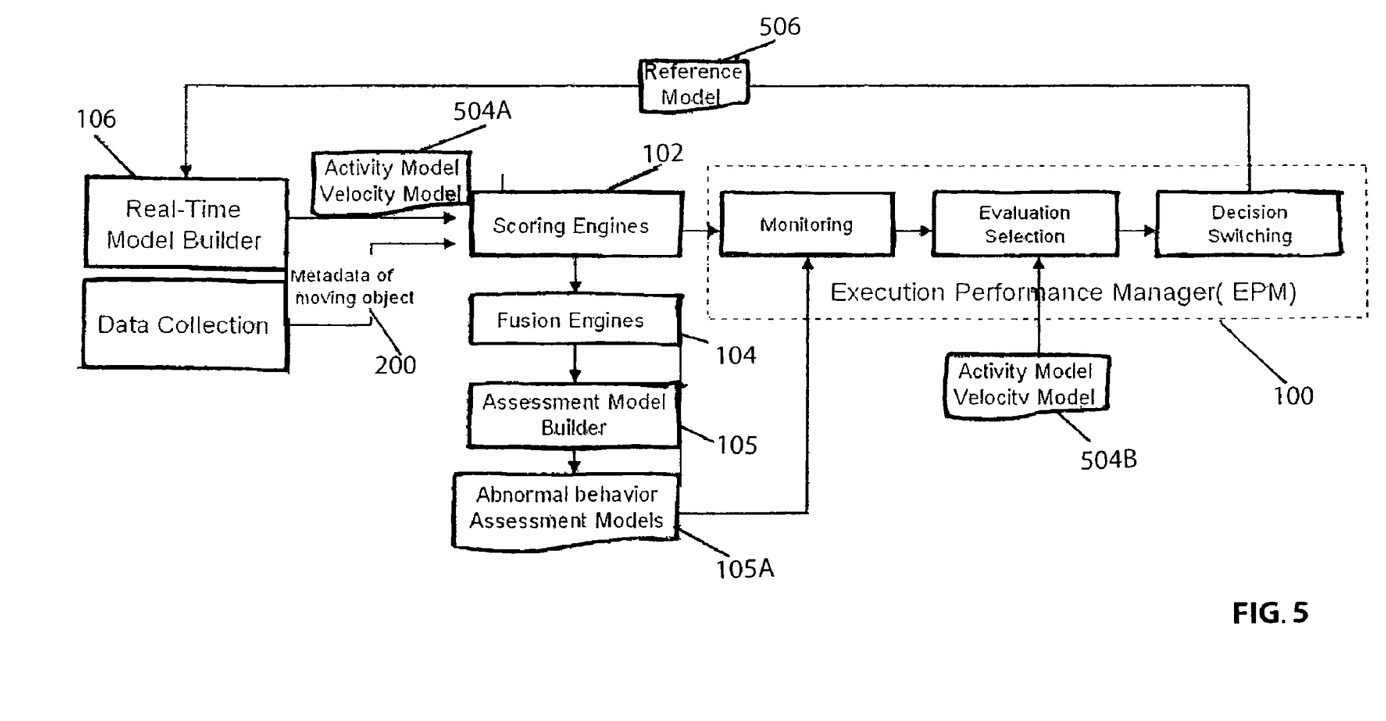
FIG. 5 is a flow diagram illustrating a process by which an EPM uses the Assessment Model built based on statistical moving object behavior scores to monitor and evaluate application context change, and uses the evaluation result to make the decision to switch the models or trigger a real time model builder to rebuild the model

Referring now to FIG. 5, the flow indicates that Scoring Engines 102 and Fusion Engines 104 gets the metadata 200 and generate the score against the motion object behavior model such as activity and velocity models 504A from Real Time model builder 106. The assessment model builder 105 builds the assessment models 105A, which captures the statistical behavior score pattern, based on the scores from Fusion Engines 104. The EPM 100 monitors the application context change using the current score against the assessment models 105A, evaluates the result of monitoring and previous activity and velocity model 504A and 504B, and selects an appropriate reference model 506 for Real Time model builder 106 or triggers real time model builder 106 to rebuild the model for the application context change.

Figure 2:
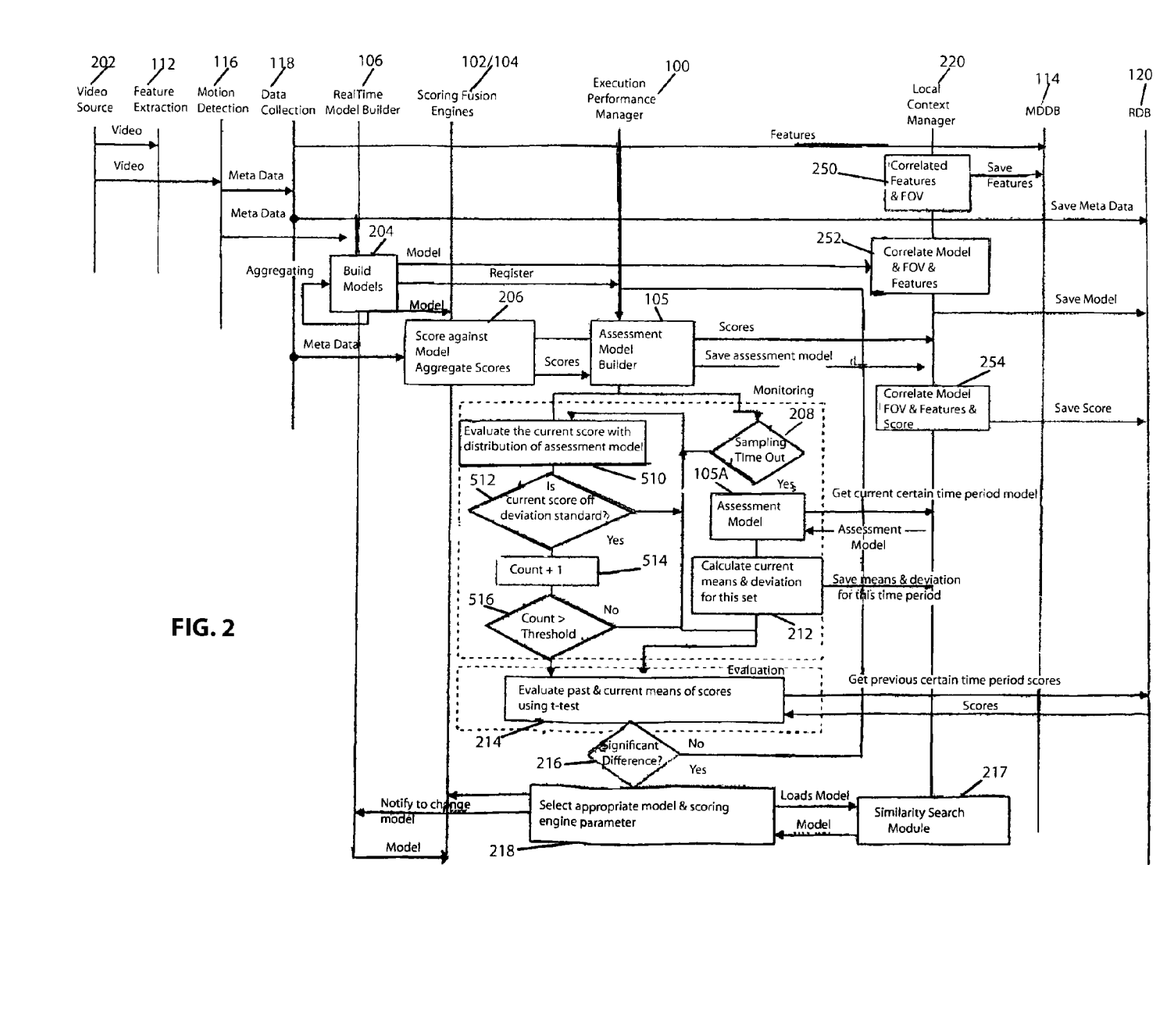
FIG. 2 is a flow diagram illustrating a process by which models are built, context aware behavior changes are detected, and models are loaded automatically in response to detection of the context aware behavior changes.

Referring now to FIG. 2, the system automatically loads a model when the system detects context behavior change. At the system startup, the Scoring Engine 102 loads configuration data and the existing model, if there is one, and waits for the metadata from Data Collection Module 118. Model builder 106 loads the configuration data from Local Context Manager 220 and waits for the Metadata from Moving Object Detection Module 116, which extracts object motion metadata from Sensor to build the model. Data Collection Module 118 waits for the Metadata from Moving Object Detection Module 116, which extracts object motion metadata from Sensor. EPM 100 waits for the registrations from Model builder 106.

A Video Source 202 depicted in FIG. 1 as Sensor 202A supplies video to Feature Extraction Module 112 and Moving Object Detection Module 116. Upon receipt of the video, Feature Extraction Module 112 extracts the features from the video, saves the features into MDDB 114, and reference of features set saves in Local Context 108 depicted in FIG. 1, which is managed by Local Context Manager 220. Likewise, Moving Object Detection Module 116 detects the moving object and sends the metadata of the moving object to Model builder 106 and Data Collection Module 118.

Upon receipt of the metadata, Model builder 106 starts to build the model at 204, registers to EPM 100, and starts two different timers for outputting the model to Local Context Manager 220 and Scoring Engine 102. The assessment model builder 105 also outputs the assessment model 105A to Local Context Manager 220. Meanwhile, EPM 100 starts a timer to monitor these models periodically and monitor score results instantaneously. It is Scoring Engine 102 that generates the scores at 206, saves the scores to Relational Data Base 120, and sends Scores to the Monitoring Module in EPM 100 and Assessment Model Builder 105. Once Model builder 106 outputs the updated model to Scoring Engine 102, Scoring Engine 102 uses the new model to score the incoming data at 206. The model builder 106 can also load a previously built model to continue enhancing the model using the new meta data inputs.

In the Monitoring Module of EPM 100, there are two monitoring threads. One thread periodically gets the previous assessment model, which captures score patterns from Local Context Manager, and monitors a current assessment model against previous same time frame assessment model. The other thread simultaneously evaluates a current score at step 510 against distribution of a scoring pattern from a previous assessment model. The Evaluation and Selection Module of EPM 100 is invoked by EPM 100 based on the Monitoring Module Result.

In the Monitoring Module, once the EPM timer is out at 208, EPM 100 gets assessment model 105A from Local Context Manager 220. EPM 100 calculates means and standard deviation of this assessment model at 212 and saves the calculated means and standard deviation in Local Context manager 220. Then, EPM 100 invokes the Evaluation and Selection Module to make a determination whether there is a previously existing assessment model within the same time frame. If there is one, the Evaluation and Selection Module in EPM 100 loads the previously existing assessment model and calculates this model's means and standard deviation. The Evaluation and Selection Module in EPM 100 uses those two sets of models' means and standard deviation to perform a test at 214 that compares their means relative to the spread or variability of their scores. This test determines whether the means are statistically different. In the other case in which data within the same time frame does not previously exist, EPM 100 saves the means and deviation into Local Context Manager 220.

In the Monitoring Module, once EPM 100 gets new scores, it evaluates the means and deviation of the previous assessment model. If the current score is determined to be off by a predefined number of standard deviations (e.g., 2 or 3 standard deviations) at decision step 512, the count is added one at 514. If the count is above a predetermined threshold within a short time frame at 516, it means that something happened to the application. EPM 100 then invokes an Evaluation and Selection Module to use previous and current assessment models' means and standard deviation to perform a test at 214 that compares their means relative to the spread or variability of their scores. This test determines whether the means are statistically different. In the other case in which data within the same time frame does not previously exist, EPM 100 saves the means and deviation into the Local Context Manager 220. The specific test method can be customized by users if specific type of adaptation is identified by the user.

Since the scores represent the activity status and patterns of moving objects, based on the results of the test, a prediction is made regarding whether the current context is changed or not. If the result of the test shows significant difference of those two means at 216, the prediction indicates that either model or behavior of moving objects change. Since the Local Context 108 for this video source 202 keeps the models on this time frame, the activities and motion patterns context as well as the image in the field of view can be evaluated. The Evaluation and Selection Module finds out whether the context is changed by communicating with Similarity Search Module 217 in Local Context Manager to do a similarity search to find a previous activity and velocity model built within a same time frame and comparing the previous models built within the same time frame first. If the result of the comparison indicates that the context-context is changed, the Evaluation and Selection Module in EPM 100 communicates with Local Context Manager 220 to load an appropriate model at 218 based on the background information of updated field of view and feature sets, and supplies the model to Model builder 106 and Scoring Engine 102. If the result of the comparison indicates that the background field of view is not changed, then a determination is made that the behavior of moving objects is changed. In this case, the Evaluation and Selection Module in the EPM 100 communicates with Local Context Manager 220 based on the scores, trajectory information, current time frame, and current model information, and loads the appropriate model at 218 to Scoring Engine 102. If Local Context Manager 220 can not find the appropriate model, EPM 100 notifies Model Builder 106 to build a new model for the current time frame.

Model Builder 106 constantly builds new models using the real-time meta data extracted from data collection module 118. Model Builder 106 receives two types of notifications from EPM 100. One type of notification indicates that the EPM 100 cannot find a similar model. In this case, the model builder builds a new model and will output the model to the scoring engine 102. The other type of notification indicates that there is a similar model that can best match to the changed context. In this case, the Model Builder 106 will merge and aggregate the currently built model with the similar model.

Referring now to FIGS. 1, 2, and 3, in order to support the adaptation of context aware behavior, a data model is needed to correlate the models 300, scoring engines 301, scores 302, features 304, matrix, time, features, and application metadata 306, and FOV 308. Local Context Manager 220 correlates features 304 and FOV 308 at 250 and stores these correlated data in MDDB 114. In addition, the time metadata is collected by data collection module 118 and supplied to the Relational Data Base 120. Local Context Manager 220 further correlates the models 300, FOV 308, and features 304 at 252 and stores these correlated data in the Relational Data Base 120. Finally, Local Context Manager 220 correlates the models 300, FOV 308, features 304, and scores 302 at 254 and stores these correlated data in the Relational Data Base 120. Thus, the data model is formed, and EPM 100 is adapted to get the appropriate model based on the data model.

Figure 4:
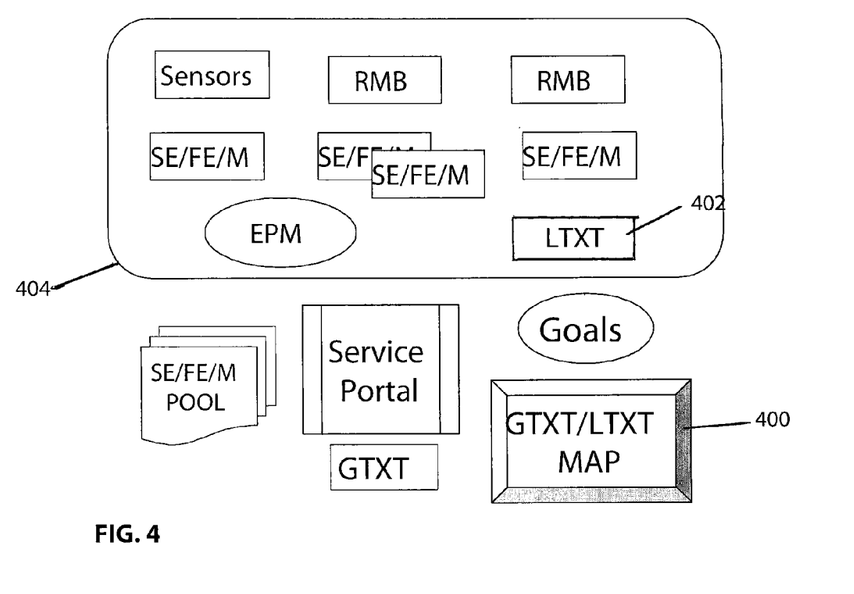
FIG. 4 is a block diagram illustrating a surveillance system implementing the architecture, process, and data model of FIGS. 1-3.

Referring now to FIG. 4, the local and global contexts are stored in LTXT/GTXT Map 400. The map 400 is multi-dimensional and supports both index as well as content search. It combines a multi-dimensional search node in the index operator to achieve a multi-level context sensitive search.

For example, the video analytic system 404 takes a snap-shot sequence of images captured from a camera as input to generate background and foreground objects. Each separated object is then processed to produce feature vectors. The set of feature vectors is used to build behavior models and stored as LTXT 402. When a new set of data is collected, it is sampled first. Then, the sampled set is scored and compared to previously stored LTXTs either based on time, sensor range, or feature set. The best matched set is selected as the primary Model for generating scores for all the input data until the next primary model is selected.

LTXT:

(ContextID, TimeProperty, SpaceProperty, Application Property, FeatureSet, Model Reference, Score Reference)—
$\rightarrow$SE/FE/M FeatureSet:—|color|motion|identity

GTXT:

Spatial and Temporal correlation between local context. For example:

$$LTXT_j = LTXT_i[TXFMMatrix]_{ij}$$

The set $\{[\text{TXFMMatrix}]_{ij}\}$ form a distributed global context that describes the linear approximation of the relationships between local context of sensor with overlapped or non-overlapped ranges.

GTXT/LTXT MAP Object:
Insert/Delete LTXT|GTXT
Put/Get LTXT|GTXT
Search LTXT|GTXT based on Context of LTXT/GTXT.

The feature set of the context is a multi-dimensional vector that can be searched based on a distance function such as L2 or L1 distance.

From the foregoing description, one skilled in the art can readily perceive that the disclosed techniques for seamless adaptation to context aware behavior models have a variety of uses and provide a number of advantages over previous surveillance systems. For example, a device can provide multiple services on demand with run-time isolation environment and resource allocation control. Also, the surveillance system includes of a set of self-organized devices without centralized management. Additionally, the surveillance system provides the infrastructure to execute surveillance data mining applications and enable those applications to collaborate with each other for threat pattern detection, trajectory and etc.

A surveillance device implementing the disclosed techniques exhibits a number of advantageous characteristics. For example, it exhibits fast and light weight execution, including an efficient data mining and scoring engine execution mechanism based on Predictive Model Descriptions. Additionally, it is capable of providing the secured run time environment to execute an application's services, such as a data mining service, a data mining scoring engine, a data collection service, a distributed directory service, etc. Also, it provides a Provide Shared Object Service to let the applications' services share the data collected by the device and to provide real time notification, which enables services and devices to collaborate. Further, it provides the Rule execution environment and in-memory cached facts to execute the application logics. Yet further, it is self-organized and is enabled to discover the community to which it belongs, discover the services that it needs to execute, and replicate the data for other devices within the community to archive fault tolerant and scalability. Finally, provides multi-level collaboration support, including a shared object service for threat, SOS for processes, and a P2P directory for isolated services in isolated communities.

A surveillance system implementing the disclosed techniques exhibits a number of advantageous characteristics. For example, it provides secured access control for each device within the community in the distributed environment. Also, it provides the distributed directory service for the community's device to discover the configuration data and services. Additionally, it provides publisher, subscriber, and notification mechanisms in the distributed environment, which enable the surveillance service provider to announce new service to the applications, upgrade/download new services and initiate new services. Further, it has scalability by distributed service proxy registration and discovery, and provides the collaboration environment for the devices, services and applications to share the knowledge and data to increase the quality services of surveillance society. Moreover, it can be rapidly deployed because it has field programmable agents supporting multiple dynamically configured video analysis and data mining services. Finally, it provides a distributed communication mechanism to enable devices and services to form their own community to achieve security, fault tolerant, and scalability.

One skilled in the art can readily appreciate that the system architecture and process achieves context aware dynamic model adaptation by employing modules to provide:

Real-time motion object behavior and abnormal behavior model building, open system management of the models, fast pre-caching of the models based on similarity of the content of the models or partial contents of the models.

Real-time abnormal behavior scoring and behavior score assessment using multiple behavior scores. Monitoring the changes of the behavior score statistics and compare it with the previously calculated scoring statistic associated with the behavior model to decide whether to switch to a new reference model to adapt to environment and application environment changes.

Perform fast search and obtain ranked order of suitable archive models and cache the model in the local context. Use the best match reference model to continue the abnormal behavior scoring engine such that the false alarm can be reduced.

One skilled in the art can also readily appreciate that the system architecture and process achieves search and adaptation to distributed context in time and space seamlessly by employing modules that:

Support collaborative model sharing using global context map. Global context map is distributed and managed in a global portal with local cache.

Manage a distributed global context map of linear transition matrix for low cost scalable data model maintaining linkage relationships between multiple local archive models, especially, in the interface areas between multiple sensors with overlapped or non-overlapped time and space ranges.

Score, rank and select suitable model using the transition matrix to fuse observations from multiple sensors.

Use the transition matrix to build estimated model from adjacent areas when there is no archive model for the area.

What is claimed is:

1. A surveillance system implementing an architecture and process to support real-time abnormal behavior assessment operations in a distributed scalable sensor network, the system comprising:
   an automated behavior model builder generating behavior models from sensor data;
   a plurality of abnormal behavior scoring engines operating concurrently to generate abnormal behavior assessment models by scoring the behavior models; and
   an execution performance manager performing fast switching of behavior models for said abnormal behavior scoring engines, wherein the execution performance manager performs fast switching between a first behavior model and a second behavior model based on a similarity between a first temporal-spatial descriptor of the first model and a second temporal-spatial descriptor of the second model,
   wherein said execution performance manager performs detection of abnormal behavior score distribution characteristic deviation by comparing a current abnormal behavior assessment model to a pre-recorded abnormal behavior assessment model, and selects a pre-recorded behavior model for said abnormal behavior scoring engines when the deviation exceeds a predetermined threshold.

2. The system of claim 1, further comprising:
   a local context manager that manages a first set of most recently used behavior models as well as a second set of behavior models that are similar to the first set of most recently used behavior models, wherein said execution performance manager selects the pre-recorded behavior model by searching the first set and the second set for similarity of the pre-recorded behavior model to a current input motion object behavior pattern.

3. The system of claim 2, wherein said local context manager implements a similarity based caching policy that pre-caches behavior model of the first set and the second set automatically match a sequence of application contexts.

4. The system of claim 1, wherein said automated behavior model builder receives moving object data, generates a current model from the moving object data in real-time, generates descriptors of the model after a preset number of trajectories, and stores the current model in a model data storage subsystem using the descriptors as indices.

5. The system of claim 4, wherein said automated behavior model builder builds multiple types of models to support dynamically loaded model builder algorithms.

6. The system of claim 5, wherein said automated behavior model builder builds an open behavior model that can be used by multiple, user-defined and dynamically loaded ones of said abnormal behavior scoring engines.

7. The system of claim 5, wherein said automated behavior model builder is a dynamically loaded model builder that builds:

a low level motion object behavior model describing normal behavior of motion patterns; and the abnormal behavior assessment model that summarizes statistical characteristics of maximal and mean abnormal behavior scores for all trajectories as an application-specific, abnormal-scoring-engine-specific context representation.

8. The system of claim 1, further comprising:

a moving object detection module detecting moving objects from the sensor data; and a data collection module communicating with said moving object detection module to get metadata, parsing the metadata to obtain parsed metadata, sending the parsed metadata to said scoring engines, and saving the parsed metadata into a model data store.

9. The system of claim 8, wherein the parsed metadata includes:

(a) object ID information; (b) center of position of object information; or (c) blob of object information.

10. The system of claim 9, wherein said automated behavior model builder generates the model based on the metadata.

11. The system of claim 1, wherein said model building module generates: (a) an activity model containing occurrence, velocity, acceleration, and speed information; and (b) a direction and speed model containing direction probability and a speed model.

12. The system of claim 1, wherein said scoring engine module keeps trajectory information of the moving objects in runtime.

13. The system of claim 1, wherein said execution performance manager makes a determination whether a background context-context has changed or behavior of one or more moving objects has changed by comparing an aggregated scores pattern of the current model to an aggregated scores pattern of one or more pre-recorded models.

14. The system of claim 1, wherein said execution performance manager makes a determination whether a background context has changed or behavior of one or more moving objects has changed by comparing the current behavior model to one or more previously archived models.

15. The system of claim 1, wherein said execution performance manager determines whether a background context has changed by comparing background features of the current behavior model with background features of a plurality of pre-recorded models built during a same time frame as the current behavior model.

16. The system of claim 15, wherein said execution performance manager selects the pre-recorded behavior model, contingent upon determination that the background context has changed, based on the background features, and otherwise selects the pre-recorded behavior model based on scores information, trajectory information, and current model information.

17. The system of claim 1, wherein said execution performance manager, upon retrieval of the pre-recorded model, runs a new set of configurations and instances of scoring engines, fusion engines, and models in parallel with a previously running set of scoring engines, fusion engines, and models, wherein outputs from the previously running set and the new set are processed concurrently to result in a smooth transition from use of the current model to use of the archived model.

18. The system of claim 1, wherein said execution performance manager retrieves the archived model by referencing a distributed global context map of one or more linear transition matrices maintaining relationships between two or more pre-recorded models each having a local context.

19. The system of claim 1, wherein said abnormal behavior scoring engines score the current model by using the transition matrix to fuse observations from multiple sensors.

20. The system of claim 1, wherein said abnormal behavior scoring engines aggregate the score results into a database, and said execution performance manager evaluates abnormality of a score pattern evidenced in the score results to detect a context change.

21. The system of claim 1, wherein said automated behavior model builder uses the transition matrix to build an estimated model from adjacent areas when there is no pre-recorded model for an area.

22. The system of claim 18, wherein the local context is a set of mappings relating context information to a recommended scoring engine, a recommended fusion engine that fuses the observations from the multiple sensors, and a recommended pre-recorded model.

23. The system of claim 22, wherein the context information specifies a context identifier, a time property, a space property, an application property, and a feature set, and the local context captures an application's contextual behaviors by linking a set features context, a temporal context, and a statistical behavior pattern.

24. The system of claim 18, wherein the global context is made up of one or more transformation relationships or probability dependency mappings between local contexts in space, time, and application.

25. The system of claim 24, wherein the global context contains a transformation matrix for an overlapped field of view.

26. The system of claim 22, wherein the global context contains a probability dependency mapping of statistical events.

27. The system of claim 1, wherein said execution performance manager searches for the pre-recorded behavior model by reference to a local context data model that relates pre-recorded behavior models, background features, and application metadata to field of view, relates the abnormal behavior scoring engines to the pre-recorded behavior models, and relates the abnormal behavior assessment models to the abnormal behavior scoring engines.

28. The system of claim 27, wherein the local context data model caches similar motion patterns and temporal and spatial descriptors, and the local context is a search descriptor said execution performance manager.

29. The system of claim 1, wherein said execution performance manager further supplies the selected pre-recorded behavior model to said automated behavior model builder.

30. The system of claim 1, wherein said model builder constantly builds behavior models based on the sensor data, and, upon said execution performance manager detecting an application context change, either loads a current built model to said scoring engines or merges the current build model with a similar model provided by said execution performance manager and loads the resulting updated model to said scoring engines.

31. A surveillance system implementing an architecture and process to support real-time abnormal behavior assessment operations in a distributed scalable sensor network, the system comprising:

an automated behavior model builder generating behavior models from sensor data;

a plurality of abnormal behavior scoring engines operating concurrently to generate abnormal behavior assessment models by scoring the behavior models;

an execution performance manager performing fast switching of behavior models for said abnormal behavior scoring engines; and a local context manager that manages a first set of most recently used behavior models as well as a second set of behavior models that are similar to the first set of most recently used behavior models, wherein said execution performance manager performs detection of abnormal behavior score distribution characteristic deviation by comparing a current abnormal behavior assessment model to a pre-recorded abnormal behavior assessment model, and selects a pre-recorded behavior model for said abnormal behavior scoring engines when the deviation exceeds a predetermined threshold, wherein said execution performance manager selects the pre-recorded behavior model by searching the first set and the second set for similarity of the pre-recorded behavior model to a current input motion object behavior pattern.

* * * * *